(12) United States Patent
Fujikura et al.

(10) Patent No.: US 6,872,706 B2
(45) Date of Patent: Mar. 29, 2005

(54) GLUCOPYRANOSYLOXYBENZYLBENZENE DERIVATIVES AND MEDICINAL COMPOSITIONS CONTAINING THE SAME

(75) Inventors: Hideki Fujikura, Nagano (JP); Nobuhiko Fushimi, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/381,846

(22) PCT Filed: Sep. 21, 2001

(86) PCT No.: PCT/JP01/08239

§ 371 (c)(1),
(2), (4) Date: Jul. 29, 2003

(87) PCT Pub. No.: WO02/28872

PCT Pub. Date: Apr. 11, 2002

(65) Prior Publication Data

US 2004/0018998 A1 Jan. 29, 2004

(30) Foreign Application Priority Data

Sep. 29, 2000 (JP) .................................. 2000-301523

(51) Int. Cl.[7] .................. A01N 43/04; A61K 31/70; C07H 15/00; C07H 17/00
(52) U.S. Cl. .................... 514/25; 514/35; 536/4.1; 536/18.1
(58) Field of Search ................ 514/25, 35; 536/4.1, 536/18.1

(56) References Cited

U.S. PATENT DOCUMENTS

| 4,598,068 A | 7/1986 | Samreth et al. |
| 5,424,406 A | 6/1995 | Tsujihara et al. |
| 5,731,292 A | 3/1998 | Tsujihara et al. |
| 6,683,056 B2 * | 1/2004 | Washburn et al. ............ 514/25 |
| 2002/0111315 A1 | 8/2002 | Washburn et al. |

FOREIGN PATENT DOCUMENTS

| EP | 0 598 359 A1 | 5/1994 |
| WO | WO 01/68660 A1 | 9/2001 |
| WO | WO 01/74834 A1 | 10/2001 |
| WO | WO 02/28872 A1 | 4/2002 |

OTHER PUBLICATIONS

Akira Oku, et al; Antidiabtic effect of T–1095, an inhibitor of Na⁺–glucose cotransporter, in nconatally streptozotocin–treated rats; European Journal of Pharmacology 391 (2000)183–192.

Mariana Panayotova–Heiermann, et al.; Sugar Binding to Na⁺/Glucose Cotransporters Is Determined by the Carboxyl–terminal Half of the Protein; The Journal of Biological Chemistry; vol. 271, No. 17, Issue of Apr. 26, 1996; pp. 10029–10034, 1996.

* cited by examiner

Primary Examiner—James O. Wilson
Assistant Examiner—Traviss C. McIntosh III
(74) Attorney, Agent, or Firm—Sughrue Mion, PLLC

(57) ABSTRACT

The present invention relates to glucopyranosyloxybenzylbenzene derivatives represented by the general formula:

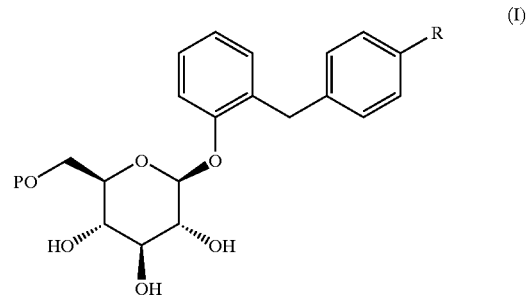

wherein P represents a group forming a prodrug; and R represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, which have an improved oral absorption and can exert an excellent inhibitory activity in human SGLT2 in vivo and which are useful as agents for the prevention or treatment of a disease associated with hyperglycemia such as diabetes, diabetic complications or obesity, and pharmaceutical compositions comprising the same.

14 Claims, No Drawings

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
atggaggagc acacagaggc                                                    20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
ggcatagaag ccccagagga                                                    20

<210> SEQ ID NO 3
<211> LENGTH: 29
<212> TYPE: DNA
<213> ORGANISM: Artificial Sequence
<220> FEATURE:
<223> OTHER INFORMATION: PCR primer

<400> SEQUENCE: 3
aacctcgaga tggaggagca cacagaggc                                          29

<210> SEQ ID NO 4
<211> LENGTH: 29
<212> TYPE: DNA
<213> ORGANISM: Artificial Sequence
<220> FEATURE:
<223> OTHER INFORMATION: PCR primer

<400> SEQUENCE: 4
aacaagcttg gcatagaagc cccagagga                                          29

<210> SEQ ID NO 5
<211> LENGTH: 25
<212> TYPE: PRT
<213> ORGANISM: Artificial Sequence
<220> FEATURE:
<223> OTHER INFORMATION: carboxy terminus of fusion protein

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25

GLUCOPYRANOSYLOXYBENZYLBENZENE DERIVATIVES AND MEDICINAL COMPOSITIONS CONTAINING THE SAME

TECHNICAL FIELD

The present invention relates to glucopyranosyloxybenzylbenzene derivatives which are useful as medicaments and pharmaceutical compositions comprising the same.

More particularly, the present invention relates to glucopyranosyloxybenzylbenzene derivatives, which are useful as agents for the prevention or treatment of a disease associated with hyperglycemia such as diabetes, diabetic complications or obesity, represented by the general formula:

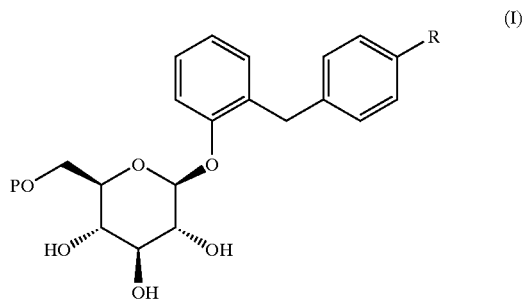

wherein P represents a group forming a prodrug; and R represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, of which glucopyranosyloxybenzylbenzene derivatives, which have an inhibitory activity in human SGLT2, represented by the general formula:

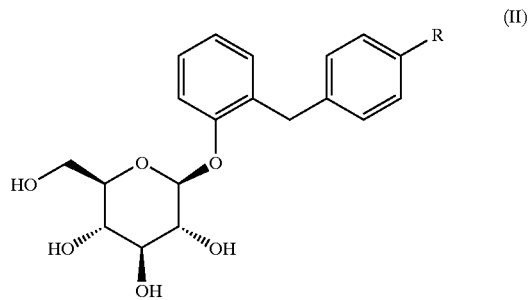

wherein R represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, are active forms, and relates to pharmaceutical compositions comprising the same.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. At present, biguanides, sulfonylureas and agents for reducing insulin resistance have been employed as antidiabetic agents. However, biguanides and sulfonylureas show occasionally adverse effects such as lactic acidosis and hypoglysemia, respectively. In case of using agents for reducing insulin resistance, adverse effects such as edema occasionally are observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510–1515 (1987)). In addition, it is reported that SGLT2 ($Na^+$/glucose cotransporter 2) is present in the S1 segment of the kidney's proximal tubule and participates mainly in reabsorption of glucose filtrated through glomerular (J. Clin. Invest., Vol. 93, pp. 397–404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents which have a potent inhibitory activity in human SGLT2 and have a new mechanism has been desired. Furthermore, since such agents promote the excretion of excess glucose though the urine and consequently the glucose accumulation in the body is decreased, they are also expected to have a preventing effect on obesity.

DISCLOSURE OF THE INVENTION

The present inventors have studied earnestly to find compounds having an inhibitory activity in human SGLT2. As a result, it was found that compounds represented by the above general formula (I) are converted in vivo into their active forms, glucopyranosyloxybenzylbenzene derivatives represented by the above general formula (II), and show an excellent inhibitory activity in human SGLT2 as mentioned below, thereby forming the basis of the present invention.

The present invention is to provide the following glucopyranosyloxybenzylbenzene derivatives which exert an inhibitory activity in human SGLT2 in vivo and show an excellent hypoglycemic effect by excreting excess glucose in the urine through preventing the reabsorption of glucose at the kidney, and pharmaceutical compositions comprising the same.

This is, the present invention relates to a glucopyranosyloxybenzylbenzene derivative represented by the general formula:

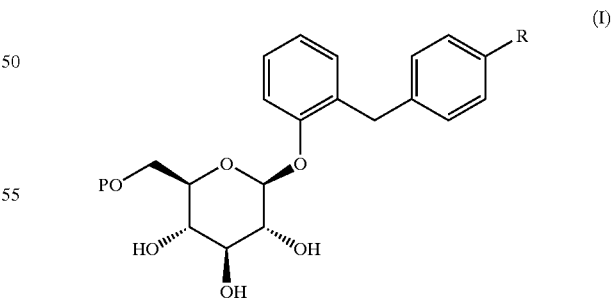

wherein P represents a group forming a prodrug; and R represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group.

The present invention relates to a pharmaceutical composition comprising as an active ingredient a glucopyranosyloxybenzylbenzene derivative represented by the above general formula (I).

The present invention relates to a human SGLT2 inhibitor comprising as an active ingredient a glucopyranosyloxybenzylbenzene derivative represented by the above general formula (I).

The present invention relates to an agent for the prevention or treatment of a disease associated with hyperglycemia, which comprises as an active ingredient a glucopyranosyloxybenzylbenzene derivative represented by the above general formula (I).

The present invention relates to a method for the prevention or treatment of a disease associated with hyperglycemia, which comprises administering a therapeutically effective amount of a glucopyranosyloxybenzylbenzene derivative represented by the above general formula (I).

The present invention relates to a use of a glucopyranosyloxybenzylbenzene derivative represented by the above general formula (I) for the manufacture of a pharmaceutical composition for the prevention or treatment of a disease associated with hyperglycemia.

In the present invention, the term "prodrug" means a compound which is converted into a glucopyranosyloxybenzylbenzene derivative represented by the above general formula (II) as an active form thereof in vivo. As examples of groups forming prodrugs, a hydroxy-protective group used generally as a prodrug, such as a lower acyl group, a lower alkoxy-substituted (lower acyl) group, a lower alkoxycarbonyl-substituted (lower acyl) group, a lower alkoxycarbonyl group and a lower alkoxy-substituted (lower alkoxycarbonyl) group, are illustrated.

Also, in the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "lower alkoxy-substituted (lower alkyl) group means the above lower alkyl group substituted by the above lower alkoxy group; the term "lower alkoxy-substituted (lower alkoxy) group means the above lower alkoxy group substituted by the above lower alkoxy group; and the term "lower alkoxy-substituted (lower alkylthio) group means the above lower alkylthio group substituted by the above lower alkoxy group. The term "lower acyl group" means a straight-chained, branched or cyclic acyl group having 2 to 7 carbon atoms such as an acetyl group, a propionyl group, a butyryl group, an isobutyryl group, a pivaloyl group, a hexanoyl group and a cyclohexylcarbonyl group; and the term "lower alkoxy-substituted (lower acyl) group means the above lower acyl group substituted by the above lower alkoxy group. The term "lower alkoxycarbonyl group" means a straight-chained, branched or cyclic alkoxycarbonyl group having 2 to 7 carbon atoms such as a methoxycarbonyl group, an ethoxycarbonyl group, an isopropyloxycarbonyl group, an isobutyloxycarbonyl group and a cyclohexyloxycarbonyl group; the term "lower alkoxycarbonyl-substituted (lower acyl) group means the above lower acyl group substituted by the above lower alkoxycarbonyl group such as a 3-(ethoxycarbonyl)propionyl group; and the term "lower alkoxy-substituted (lower alkoxycarbonyl) group means the above lower alkoxycarbonyl group substituted by the above alkoxy group such as a 2-methoxyethoxycarbonyl group.

In the substituent R, a lower alkyl group and a lower alkoxy group are preferable, a straight-chained or branched alkyl group having 1 to 4 carbon atoms and a straight-chained or branched alkoxy group having 1 to 3 carbon atoms are more preferable, and an ethyl group and a methoxy group are most preferable. In the substituent P, a lower acyl group and a lower alkoxycarbonyl group are preferable. As the lower acyl group, a straight-chained or branched acyl group having 4 to 6 carbon atoms is preferable, and a butyryl group and a hexanoyl group are more preferable. As the lower alkoxycarbonyl group, a straight-chained or branched alkoxycarbonyl group having 2 to 5 carbon atoms is preferable, and a methoxycarbonyl group and an ethoxycarbonyl group are more preferable.

The compounds of the present invention can be prepared by introducing a hydroxy-protective group being capable of using commonly in prodrugs into the hydroxy group of a glucopyranosyl-oxybenzylbenzene derivative represented by the above general formula (II) in the usual way. For example, the compounds represented by the above general formula (I) of the present invention can be prepared using a glucopyranosyloxybenzylbenzene derivative represented by the above general formula (II) according to the following procedure:

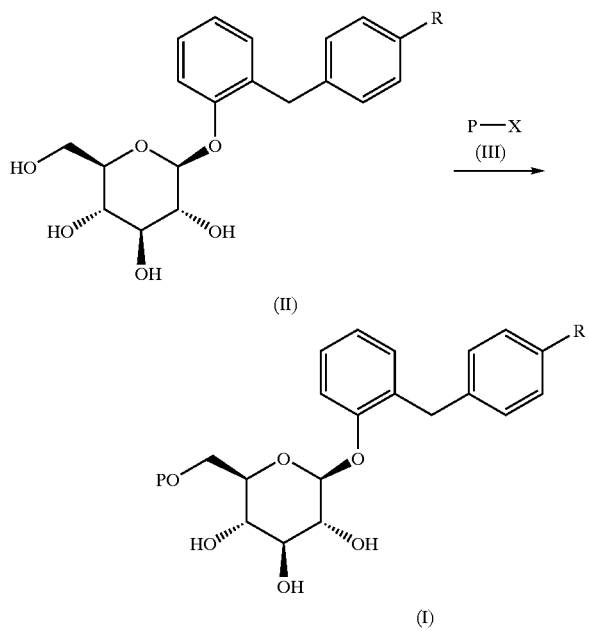

wherein X represents a leaving group such as a bromine atom and a chlorine atom; and R and P have the same meanings as defined above.

A prodrug represented by the above general formula (I) can be prepared by protecting the hydroxy group of a glucopyranosyloxybenzylbenzene derivative represented by the above general formula (II) with a reagent for protecting represented by the above general formula (III) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent. As the solvent used, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually from 30 minutes to 2 days, varying based on a used starting material, solvent and reaction temperature.

For example, the compounds represented by the above general formula (II) of the present invention which are used as starting materials in the aforementioned production process can be prepared according to the following procedure:

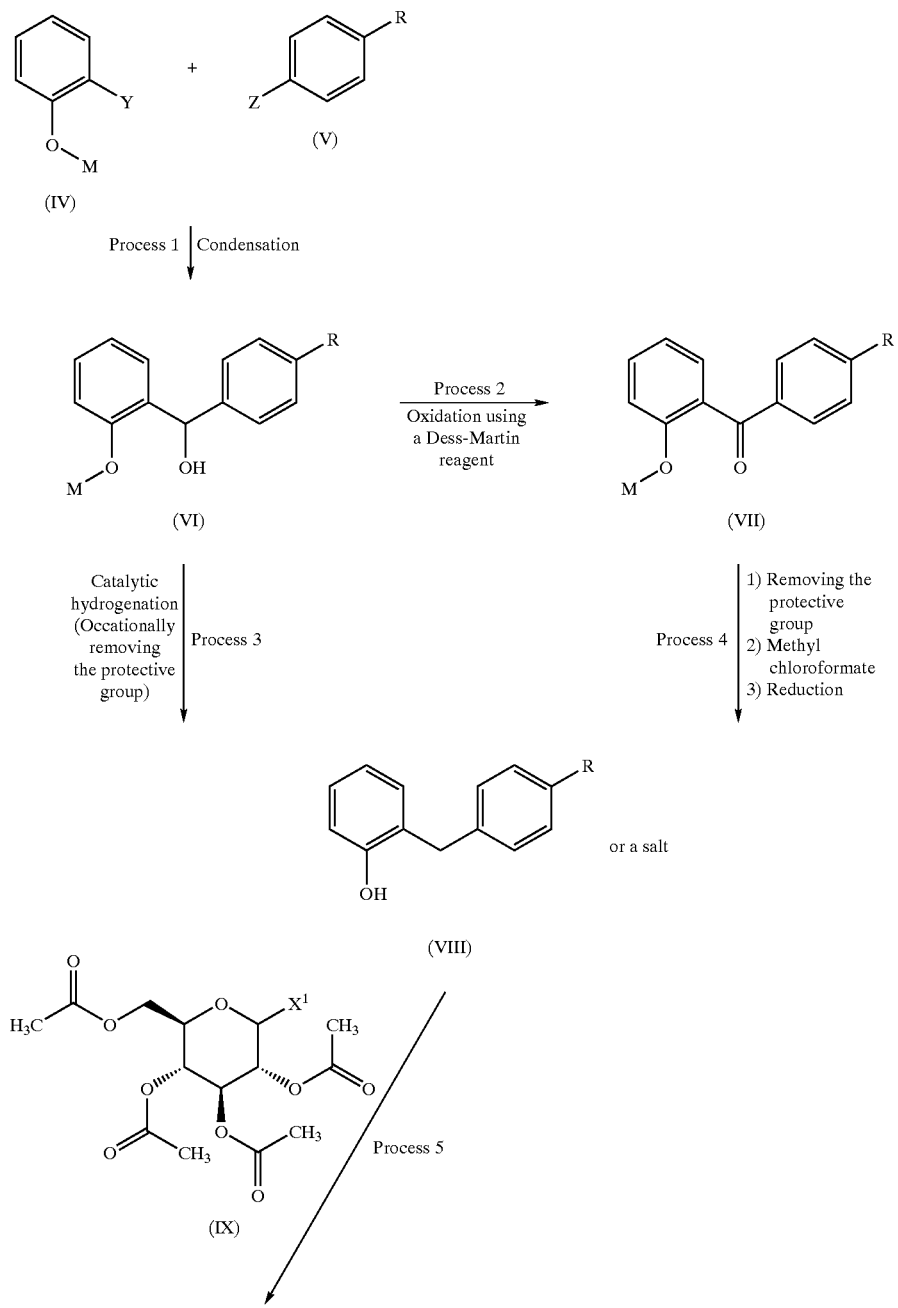

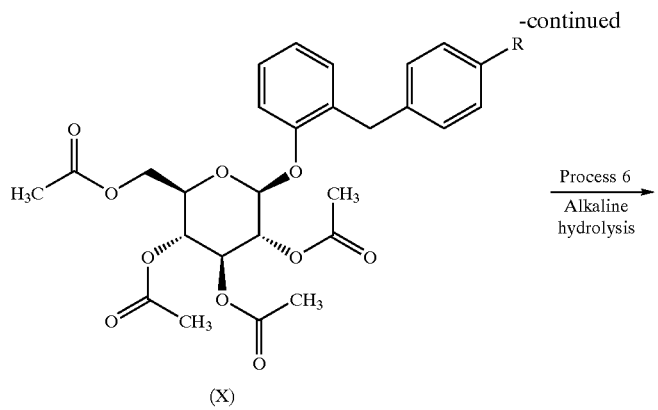

(X)

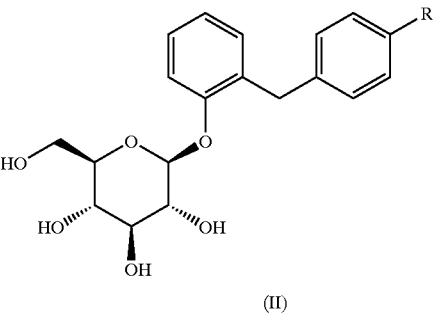

(II)

wherein M represents a hydroxy-protective group; $X^1$ represents a leaving group such as a trichloroacetoimidoyloxy group, an acetoxy group, a bromine atom or a fluorine atom; one of Y and z represents MgBr, MgCl, MgI or a lithium atom, while the other represents a formyl group; and R has the same meaning as defined above.

Process 1

A compound represented by the above general formula (VI) can be prepared by condensing a benzaldehyde derivative represented by the above general formula (IV) with a Grignard reagent or a lithium reagent represented by the above general formula (V), or by condensing a Grignard reagent or a lithium reagent represented by the above general formula (IV) with a benzaldehyde derivative represented by the above general formula (V) in an inert solvent. As the solvent used, tetrahydrofuran, diethyl ether, a mixed solvent thereof and the like can be illustrated. The reaction temperature is usually from −78° C. to reflux temperature, and the reaction time is usually from 10 minutes to 1 day, varying based on a used starting material, solvent and reaction temperature.

Process 2

A compound represented by the above general formula (VII) can be prepared by subjecting a compound represented by the above general formula (VI) to oxidation using a Dess-Martin reagent in an inert solvent. As the solvent used, dichloromethane, chloroform, acetonitrile, a mixed solvent thereof and the like can be illustrated. The reaction temperature is usually from 0° C. to reflux temperature, and the reaction time is usually from 1 hour to 1 day, varying based on a used starting material, solvent and reaction temperature.

Process 3

A compound represented by the above general formula (VIII) can be prepared by subjecting a compound represented by the above general formula (VI) to catalytic hydrogenation using a palladium catalyst such as palladium-carbon powder in the presence or absence of an acid such as hydrochloric acid in an inert solvent, and removing a protective group in the usual way as occasion demands. As the solvent used in the catalytic hydrogenation, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. The compound of the above general formula (VIII) can be converted into a salt thereof such as a sodium salt or a potassium salt in the usual way.

Process 4

A compound represented by the above general formula (VIII) can be prepared by removing the protective group M of a compound represented by the above general formula (VII) in the usual way, condensing the resulting compound with methyl chloroformate in the presence of a base such as triethylamine, diisopropyl-ethylamine or 4-(N,N-dimethylamino)pyridine in an inert solvent and subjecting the resulting carbonate compound to reduction using a reducing agent such as sodium borohydride. As the solvent used in the condensing reaction, tetrahydrofuran, dichloromethane, acetonitrile, ethyl acetate, diethyl ether, a mixed solvent thereof and the like can be illustrated. The reaction temperature is usually from 0° C. to reflux temperature, and the reaction time is usually from 30 minutes to 1 day, varying based on a used starting material, solvent and reaction temperature. As the solvent used in the reducing reaction, a mixed solvent with tetrahydrofuran and water, and the like can be illustrated. The reaction temperature is usually from 0° C. to reflux temperature, and the reaction time is usually from 1 hour to 1 day, varying based on a used starting material, solvent and reaction temperature. The compound of the above general formula (VIII) can be converted into a salt thereof such as a sodium salt or a potassium salt in the usual way.

Process 5

A glucoside represented by the above general formula (X) can be prepared by subjecting a benzylphenol derivative represented by the above general formula (VIII) or a salt thereof to glycosidation using a glycosyl-donor represented by the above general formula (IX) such as 2,3,4,6-tetra-O-acetyl-1-O-trichloroacetoimidoyl-α-D-glucopyranose, 1,2,3,4,6-penta-O-acetyl-β-D-glucopyranose, 2,3,4,6-tetra-O-acetyl-α-D-glucopyranosyl bromide and 2,3,4,6-tetra-O-acetyl-β-D-glucopyranosyl fluoride in the presence of an activating reagent such as boron trifluoride diethyl ether complex, silver trifluoromethanesulfonate, tin(IV) chloride or trimethylsilyl trifluoromethanesulfonate in an inert solvent. As the solvent used, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting meterial, solvent and reaction temperature.

Process 6

A glucopyranosyloxybenzylbenzene derivative represented by the above general formula (II) can be prepared by subjecting a glucoside represented by the above general formula (X) to alkaline hydrolysis to remove the hydroxy-protective groups. As the solvent used, water, methanol, ethanol, tetrahydrofuran, a mixed solvent thereof and the like can be illustrated, and as alkaline materials, sodium hydroxide, sodium methoxide, sodium ethoxide or the like can be used. The treatment temperature is usually from 0° C. to reflux temperature, and the treatment time is usually from 30 minutes to 6 hours, varying based on a used starting material, solvent and treatment temperature.

The compounds of the present invention obtained by the above production process can be isolated and purified by conventional separation means such as fractional recrystallization, purification using chromatography, solvent extraction and solid phase extraction.

The prodrugs represented by the above general formula (I) of the present invention include their hydrates and their solvates with pharmaceutically acceptable solvents such as ethanol.

The prodrug represented by the above general formula (I) of the present invention is converted into a glucopyranosyloxybenzylbenzene derivative represented by the above general formula (II) as an active form thereof in vivo and can exert an excellent inhibitory activity in human SGLT2. In addition, the prodrugs represented by the above general formula (I) of the present invention have an improved oral absorption, and pharmaceutical compositions comprising as the active ingredient the prodrug have a highly usefulness as oral formulations. Therefore, the prodrugs of the present invention are extremely useful as agents for the prevention or treatment of a disease associated with hyperglycemia such as diabetes, diabetic complications, obesity or the like.

When the pharmaceutical compositions of the present invention are employed in the practical treatment, various dosage forms are used depending on their uses. As examples of the dosage forms, powders, granules, fine granules, dry sirups, tablets, capsules, injections, solutions, ointments, suppositories, poultices and the like are illustrated, which are orally or parenterally administered.

These pharmaceutical compositions can be prepared by admixing with or by diluting and dissolving with an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with pharmaceutically conventional methods depending on their dosage forms.

When the pharmaceutical compositions of the present invention are employed in the practical treatment, the dosage of a compound of the present invention as the active ingredient is appropriately decided depending on the age, sex, body weight and degrees of symptoms and treatment of each patient, which is approximately within the range of from 0.1 to 1,000 mg per day per adult human in case of oral administration and approximately within the range of from 0.01 to 300 mg per day per adult human in case of parenteral administration, and the daily dose can be divided into one to several doses per day and administered suitably.

EXAMPLES

The present invention is further illustrated in more detail by way of the following Reference Examples, Examples and Test Examples. However, the present invention is not limited thereto.

Reference Example 1

2-(4-Isobutylbenzyl)phenol

A Grignard reagent was prepared from 2-benzyloxy-1-bromobenzene (0.20 g), magnesium (0.026 g), a catalytic amount of iodine and tetrahydrofuran (1 mL) in the usual manner. The obtained Grignard reagent was added to a solution of 4-isobutylbenzaldehyde (0.16 g) in tetrahydrofuran (2 mL), and the mixture was stirred at room temperature for 30 minutes. The reaction mixture was purified by column chromatography on aminopropyl silica gel (eluent: tetrahydrofuran) to give a diphenylmethanol compound (0.23 g). The obtained diphenyl-methanol compound was dissolved in ethanol (3 mL) and concentrated hydrochloric acid (0.1 mL). To the solution was added a catalytic amount of 10% palladium-carbon powder, and the mixture was stirred under a hydrogen atmosphere at room temperature overnight. The catalyst was removed by filtration, and the filtrate was concentrated under reduced pressure. The residue was purified by column chromatography on silica gel (eluent: dichloromethane/hexane=1/1) to give 2-(4-isobutylbenzyl)phenol (0.10 g).

$^1$H-NMR (CDCl$_3$) δ ppm: 0.89 (6H, d, J=6.6 Hz), 1.75–1.90 (1H, m), 2.43 (2H, d, J=7.2 Hz), 3.97 (2H, s), 4.66 (1H, s), 6.75–6.85 (1H, m), 6.85–6.95 (1H, m), 7.00–7.20 (6H, m)

Reference Example 2

2-(4-Isopropoxybenzyl)phenol

The title compound was prepared in a similar manner to that described in Reference Example 1 using 4-isopropoxybenzaldehyde instead of 4-isobutylbenzaldehyde.

$^1$H-NMR (CDCl$_3$) δ ppm: 1.31 (6H, d, J=6.1 Hz), 3.93 (2H, s), 4.50 (1H, heptet, J=6.1 Hz), 4.72 (1H, s), 6.75–6.85 (3H, m), 6.85–6.95 (1H, m), 7.05–7.20 (4H, m)

Reference Example 3

2-(4-Ethoxybenzyl)phenol

A Grignard reagent was prepared from 1-bromo-4-ethoxybenzene (1.5 g), magnesium (0.19 g), a catalytic amount of iodine and tetrahydrofuran (2 mL) in the usual manner. To the obtained Grignard reagent solution was added dropwise a solution of 2-benzyloxybenzaldehyde (1.1 g) in tetrahydrofuran (15 mL), and the mixture was stirred at room temperature for 30 minutes. To the reaction mixture were added a saturated aqueous ammonium chloride solution (10 mL) and water (20 mL), and the mixture was extracted with ethyl acetate (100 mL). The extract was washed with water (20 mL) and brine (20 mL), and dried over anhydrous sodium sulfate. Thereafter, the solvent was removed under reduced pressure. The residue was purified by column chromatography on silica gel (eluent: hexane/ethyl acetate=5/1) to give a diphenylmethanol compound (1.7 g). The obtained diphenylmethanol compound (1.7 g) was dissolved in ethanol (25 mL). To the solution were added concentrated hydrochloric acid (0.42 mL) and a catalytic amount of 10% palladium-carbon powder, and the mixture was stirred under a hydrogen atmosphere at room temperature for 18 hours. The catalyst was removed by filtration, and the filtrate was concentrated under reduced pressure. To the residue was added ethyl acetate (100 mL), and the mixture was washed with a saturated aqueous sodium hydrogen carbonate solution (30 mL) and brine (30 mL). The organic layer was dried over anhydrous sodium sulfate, and the solvent was removed under reduced pressure. The residue was purified by column chromatography on silica gel (eluent: hexane/ethyl acetate=8/1) to give 2-(4-ethoxybenzyl)phenol (0.85 g).

$^1$H-NMR (CDCl$_3$) δ ppm: 1.39 (3H, t, J=7.1 Hz), 3.93 (2H, s), 4.00 (2H, q, J=7.1 Hz), 4.72 (1H, s), 6.75–6.85 (3H, m), 6.85–6.95 (1H, m), 7.05–7.20 (4H, m)

Reference Example 4

2-(4-Ethylthiobenzyl)phenol

A Grignard reagent was prepared from 1-bromo-4-ethyl-thiobenzene (1.1 g), magnesium (0.12 g), a catalytic amount of iodine and tetrahydrofuran (5 mL) in the usual manner. To the obtained Grignard reagent solution was added a solution of 2-(methoxymethoxy)benzaldehyde (0.56 g) in tetrahydrofuran (12 mL), and the mixture was stirred at 65° C. for 10 minutes. After cooling to ambient temperature, a saturated aqueous ammonium chloride solution (5 mL) and water (20 mL) were added to the reaction mixture, and the mixture was extracted with ethyl acetate (80 mL). The extract was washed with water (20 mL) and brine (20 mL), dried over anhydrous sodium sulfate, then the solvent was removed under reduced pressure. The residue was purified by column chromatography on silica gel (eluent: hexane/ethyl acetate=4/1) to give a diphenylmethanol compound (0.91 g). The obtained diphenylmethanol compound (0.90 g) was dissolved in dichloromethane (15 mL). To the solution was added a Dess-Martin reagent (1,1,1-tris(acetyloxy)-1,1-dihydro-1,2-benziodoxol-3-(1H)-one) (1.5 g), and the mixture was stirred at 25° C. for 26 hours. To the reaction mixture were added diethyl ether (75 mL) and 1 mol/L aqueous sodium hydroxide solution (30 mL), the mixture was stirred vigorously, and the organic layer was separated. The organic layer was washed with 1 mol/L aqueous sodium hydroxide solution (30 mL), water (30 mL, 3 times) and brine (30 mL), dried over anhydrous sodium sulfate, and the solvent was removed under reduced pressure. The residue was purified by column chromatography on silica gel (eluent: hexane/ethyl acetate=15/1–9/1) to afford a ketone compound (0.82 g). A mixture of the obtained ketone compound (0.81 g), p-toluene-sulfonic acid monohydrate (0.10 g) and methanol (14 mL) was stirred at 60° C. for 4 hours. After cooling to ambient temperature, the reaction mixture was concentrated under reduced pressure. The residue was purified by column chromatography on silica gel (eluent: hexane/ethyl acetate=15/1) to give a deprotected compound (0.69 g). The obtained deprotected compound (0.68 g) was dissolved in tetrahydrofuran (11 mL), triethylamine (0.41 mL) and methyl chloroformate (0.22 mL) were added to the solution, and the mixture was stirred at 25° C. for 1 hour. Furthermore, triethylamine (0.1 mL) and methyl chloroformate (0.061 mL) were added to the reaction mixture, and the mixture was stirred for 30 minutes. The reaction mixture was filtered, and the filtrate was concentrated under reduced pressure. The residue was dissolved in tetrahydrofuran (14 mL) and water (7 mL), sodium borohydride (0.40 g) was added to the solution, and the mixture was stirred at 25° C. for 7 hours. To the reaction mixture was added dropwise 1 mol/L hydrochloric acid (15 mL), and the mixture was extracted with ethyl acetate (75 mL). The extract was washed with water (20 mL), a saturated aqueous sodium hydrogen carbonate solution (20 mL) and brine (20 mL), dried over anhydrous sodium sulfate, and the solvent was removed under reduced pressure. The residue was purified by column chromatography on silica gel (eluent: hexane/ethyl acetate=8/1) to give 2-(4-ethyl-thiobenzyl)phenol (0.62 g).

$^1$H-NMR (CDCl$_3$) δ ppm: 1.29 (3H, t, J=7.3 Hz), 2.90 (2H, q, J=7.3 Hz), 3.96 (2H, s), 4.62 (1H, s), 6.75–6.80 (1H, m), 6.85–6.95 (1H, m), 7.05–7.20 (4H, m), 7.20–7.30 (2H, m)

Reference Example 5

2-(4-Methoxybenzyl)phenyl 2,3,4,6-tetra-O-acetyl-β-D-glucopyranoside

To a solution of 2-(4-methoxybenzyl)phenol (46 mg) and 2,3,4,6-tetra-O-acetyl-1-O-trichloroacetoimdoyl-α-D-glucopy ranose (0.13 g) in dichloromethane (2 mL) was added boron trifluoride diethyl ether complex (0.033 mL), and the mixture was stirred at room temperature for 1 hour. The reaction mixture was purified by column chromatography on aminopropyl silica gel (eluent: dichloromethane) to give 2-(4-methoxybenzyl)phenyl 2,3,4,6-terta-O-acetyl-β-D-glucopyranoside (0.11 g).

$^1$H-NMR (CDCl$_3$) δ ppm: 1.91 (3H, s), 2.03 (3H, s), 2.05 (3H, s), 2.08 (3H, s), 3.77 (3H, s), 3.80–3.95 (3H, m), 4.17 (1H, dd, J=2.5, 12.2 Hz), 4.29 (1H, dd, J=5.5, 12.2 Hz), 5.11 (1H, d, J=7.5 Hz), 5.10–5.25 (1H, m), 5.25–5.40 (2H, m), 6.75–6.85 (2H, m), 6.95–7.10 (5H, m), 7.10–7.25 (1H, m)

Reference Example 6

2-(4-Methylbenzyl)phenyl 2,3,4,6-tetra-O-acetyl-β-D-glucopyranoside

The title compound was prepared in a similar manner to that described in Reference Example 5 using 2-(4-methylbenzyl)-phenol instead of 2-(4-methoxybenzyl)phenol.

$^1$H-NMR (CDCl$_3$) δ ppm: 1.89 (3H, s), 2.03 (3H, s), 2.05 (3H, s), 2.07 (3H, s), 2.30 (3H, s), 3.80–3.95 (3H, m), 4.17 (1H, dd, J=2.5, 12.3 Hz), 4.28 (1H, dd, J=5.5, 12.3 Hz), 5.11 (1H, d, J=7.5 Hz), 5.10–5.25 (1H, m), 5.25–5.40 (2H, m), 6.90–7.20 (8H, m)

Reference Example 7

2-(4-Ethylbenzyl)phenyl 2,3,4,6-tetra-O-acetyl-β-D-glucopyranoside

The title compound was prepared in a similar manner to that described in Reference Example 5 using 2-(4-ethylbenzyl)-phenol instead of 2-(4-methoxybenzyl)phenol.

$^1$H-NMR (CDCl$_3$) δ ppm: 1.20 (3H, t, J=7.6 Hz), 1.87 (3H, s), 2.03 (3H, s), 2.05 (3H, s), 2.08 (3H, s), 2.60 (2H, q, J=7.6 Hz), 3.80–4.00 (3H, m), 4.18 (1H, dd, J=2.3, 12.2 Hz), 4.28 (1H, dd, J=5.4, 12.2 Hz), 5.11 (1H, d, J=7.5 Hz), 5.10–5.25 (1H, m), 5.25–5.40 (2H, m), 6.90–7.25 (8H, m)

Reference Example 8

2-(4-Isobutylbenzyl)phenyl 2,3,4,6-tetra-O-acetyl-α-D-glucopyranoside

The title compound was prepared in a similar manner to that described in Reference Example 5 using 2-(4-isobutylbenzyl)phenol instead of 2-(4-methoxybenzyl)phenol.

$^1$H-NMR (CDCl$_3$) δ ppm: 0.88 (6H, d, J=6.6 Hz), 1.75–1.90 (1H, m), 1.87 (3H, s), 2.03 (3H, s), 2.05 (3H, s), 2.08 (3H, s), 2.42 (2H, d, J=7.2 Hz), 3.80–3.95 (3H, m), 4.18 (1H, dd, J=2.4, 12.3 Hz), 4.29 (1H, dd, J=5.5, 12.3 Hz), 5.11 (1H, d, J=7.6 Hz), 5.10–5.25 (1H, m), 5.25–5.40 (2H, m), 6.90–7.25 (8H, m)

Reference Example 9

2-(4-Ethoxybenzyl)phenyl 2,3,4,6-tetra-O-acetyl-β-D-glucopyranoside

The title compound was prepared in a similar manner to that described in Reference Example 5 using 2-(4-ethoxybenzyl)phenol instead of 2-(4-methoxybenzyl)phenol.

$^1$H-NMR (CDCl$_3$) δ ppm: 1.39 (3H, t, J=7.0 Hz), 1.91 (3H, s), 2.03 (3H, s), 2.05 (3H, s), 2.07 (3H, s), 3.80–3.95 (3H, m), 3.99 (2H, q J=7.0 Hz), 4.18 (1H, dd, J=2.5, 12.3 Hz), 4.28 (1H, dd, J=5.6, 12.3 Hz), 5.10 (1H, d, J=7.7 Hz), 5.15–5.25 (1H, m), 5.25–5.40 (2H, m), 6.75–6.85 (2H, m), 6.95–7.10 (5H, m), 7.10–7.20 (1H, m)

Reference Example 10

2-(4-Isopropoxybenzyl)phenyl 2,3,4,6-tetra-O-acetyl-β-D-glucopyranoside

The title compound was prepared in a similar manner to that described in Reference Example 5 using 2-(4-isopropoxy-benzyl)phenol instead of 2-(4-methoxybenzyl) phenol.

$^1$H-NMR (CDCl$_3$) δ ppm: 1.30 (6H, d, J=6.0 Hz), 1.90 (3H, s), 2.03 (3H, s), 2.05 (3H, s), 2.08 (3H, s), 3.80–3.90 (3H, m), 4.18 (1H, dd, J=2.3, 12.3 Hz), 4.28 (1H, dd, J=5.5, 12.3 Hz), 4.48 (1H, heptet, J=6.0 Hz), 5.10 (1H, d, J=7.7 Hz), 5.10–5.25 (1H, m), 5.25–5.40 (2H, m), 6.70–6.85 (2H, m), 6.90–7.10 (5H, m), 7.10–7.20 (1H, m)

Reference Example 11

2-(4-Methoxybenzyl)phenyl β-D-glucopyranoside

Sodium methoxide (28% methanol solution; 0.12 mL) was added to a solution of 2-(4-methoxybenzyl)phenyl 2,3,4,6-tetra-O-acetyl-β-D-glucopyranoside (0.11 g) in methanol (4 mL), and the mixture was stirred at room temperature for 30 minutes. The solvent was removed under reduced pressure. The residue was purified by column chromatography on silica gel (eluent: dichloromethane/methanol=10/1) to give 2-(4-methoxybenzyl)-phenyl β-D-glucopyranoside (65 mg).

$^1$H-NMR (CD$_3$OD) δ ppm: 3.35–3.55 (4H, m), 3.69 (1H, dd, J=5.1, 12.1 Hz), 3.73 (3H, s), 3.80–4.00 (2H, m), 4.03 (1H, d, J=15.1 Hz), 4.91 (1H, d, J=7.4 Hz), 6.75–6.85 (2H, m), 6.85–6.95 (1H, m), 6.95–7.10 (1H, m), 7.10–7.20 (4H, m)

Reference Example 12

2-(4-Methylbenzyl)phenyl β-D-glucopyranoside

The title compound was prepared in a similar manner to that described in Reference Example 11 using 2-(4-methylbenzyl)-phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm: 2.27 (3H, s), 3.35–3.55 (4H, m), 3.69 (1H, dd, J=5.2, 12.0 Hz), 3.80–3.90 (1H, m), 3.94 (1H, d, J=15.0 Hz), 4.05 (1H, d, J=15.0 Hz), 4.85–4.95 (1H, m), 6.85–6.95 (1H, m), 6.95–7.20 (7H, m)

Reference Example 13

2-(4-Ethylbenzyl)phenyl β-D-glucopyranoside

The title compound was prepared in a similar manner to that described in Reference Example 11 using 2-(4-ethylbenzyl)-phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm: 1.15–1.25 (3H, m), 2.50–2.65 (2H, m), 3.35–3.55 (4H, m), 3.65–3.75 (1H, m), 3.80–4.00 (2H, m), 4.06 (1H, d, J=14.9 Hz), 4.85–5.00 (1H, m), 6.85–7.00 (1H, m), 7.00–7.20 (7H, m)

Reference Example 14

2-(4-Isobutylbenzyl)phenyl β-D-glucopyranoside

The title compound was prepared in a similar manner to that described in Reference Example 11 using 2-(4-isobutyl-benzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm: 0.80–0.95 (6H, m), 1.70–1.90 (1H, m), 2.41 (2H, d, J=7.1 Hz), 3.30–3.55 (4H, m), 3.60–3.75 (1H, m), 3.80–3.95 (1H, m), 3.95 (1H, d, J=15.0 Hz), 4.06 (1H, d, J=15.0 Hz), 4.85–4.95 (1H, m), 6.80–7.20 (8H, m)

Reference Example 15

2-(4-Ethoxybenzyl)phenyl β-D-glucopyranoside

The title compound was prepared in a similar manner to that described in Reference Example 11 using 2-(4-ethoxybenzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm: 1.35 (3H, t, J=6.8 Hz), 3.35–3.55 (4H, m), 3.60–3.75 (1H, m), 3.80–4.10 (5H, m), 4.90 (1H, d, J=7.1 Hz), 6.70–6.85 (2H, m), 6.85–6.95 (1H, m), 7.00–7.20 (5H, m)

Reference Example 16

2-(4-Isopropoxybenzy)phenyl β-D-Glucopyranoside

The title compound was prepared in a similar manner to that described in Reference Example 11 using 2-(4-isopropoxyl-benzyl)phenyl 2,3,4,6-tetra-O-acetyl-β-D-glucopyranoside instead of 2-(4-methoxybenzyl)phenyl 2,3,4,6-tetra-O-acetyl-β-D-glucopyranoside.

$^1$H-NMR (CD$_3$OD) δ ppm: 1.27 (6H, d, J=6.0 Hz), 3.35–3.55 (4H, m), 3.69 (1H, dd, J=5.4, 12.1 Hz), 3.88 (1H, dd, J=2.0, 12.1 Hz), 3.91 (1H, d, J=15.0 Hz), 4.02 (1H, d, J=15.0 Hz), 4.51 (1H, heptet, J=6.0 Hz), 4.91 (1H, d, J=7.7 Hz), 6.70–6.85 (2H, m), 6.85–6.95 (1H, m), 7.00–7.10 (1H, m), 7.10–7.20 (4H, m)

Reference Example 17

2-(4-Ethylthiobenzyl)phenyl β-D-glucopyranoside

To a solution of 2-(4-ethylthiobenzyl)phenol (0.51 g) and 1,2,3,4,6-penta-O-acetyl-β-D-glucopyranose (2.4 g) in toluene (6.3 mL) and dichloromethane (2.7 mL) was added boron trifluoride diethyl ether complex (0.78 mL), and the mixture was stirred at room temperature for 9 hours. To the reaction mixture were added ethyl acetate (70 mL) and a saturated aqueous sodium hydrogen carbonate solution (25 mL), and the organic layer was separated. The organic layer was washed with brine (25 mL), dried over anhydrous sodium sulfate, and the solvent was removed under reduced pressure. The residue was dissolved in methanol (10.5 mL), sodium methoxide (28% methanol solution; 0.08 mL) was added to the solution, and the mixture was stirred at 25° C. for 18 hours. To the reaction mixture were added ethylacetate (75 mL) and water (20 mL), and the organic layer was separated. The organic layer was washed with brine (20 mL), dried over anhydrous sodium sulfate, and the solvent was removed under reduced pressure. The residue was purified by column chromatography on silica gel (eluent: dichloromethane/methanol=10/1). The solvent was removed under reduced pressure, diethyl ether was added to the residue, and the resulting precipitates were collected by filtration. The obtained colorless solid was washed with diethyl ether and dried under reduced pressure to give 2-(4-ethylthiobenzyl)phenylβ-D-glucopyranoside (0.51 g).

$^1$H-NMR (CD$_3$OD) δ ppm: 1.24 (3H, t, J=7.3 Hz), 2.88 (2H, q, J=7.3 Hz), 3.35–3.55 (4H, m), 3.69 (1H, dd, J=5.0, 12.2 Hz), 3.88 (1H, dd, J=2.0, 12.2 Hz), 3.95 (1H, d, J=15.1 Hz), 4.08 (1H, d, J=15.1 Hz), 4.91 (1H, d, J=7.3 Hz), 6.85–7.00 (1H, m), 7.00–7.10 (1H, m), 7.10–7.30 (6H, m)

Example 1

2-(4-Methoxybenzyl)phenyl 6-O-ethoxycarbonyl-β-D-glucopyranoside

To a solution of 2-(4-methoxybenzyl)phenyl β-D-glucopyranoside (0.075 g) in 2,4,6-trimethylpyridine (2 mL) was added ethyl chloroformate (0.04 mL) at room temperature. After the mixture was stirred at room temperature for 16 hours, a saturated aqueous citric acid solution was added to the reaction mixture, and the mixture was extracted with ethyl acetate. The extract was washed with water and dried over anhydrous magnesium sulfate, and the solvent was removed under reduced pressure. The residue was purified by preparative thin layer chromatography on silica gel (eluent: dichloromethane/methanol=10/1) to give amorphous 2-(4-methoxybenzyl)phenyl 6-O-ethoxycarbonyl-β-D-glucopyranoside (0.032 g).

$^1$H-NMR (CD$_3$OD) δ ppm: 1.23 (3H, t, J=7.1 Hz), 3.30–3.65 (4H, m), 3.74 (3H, s), 3.93 (1H, d, J=15.1 Hz), 4.02 (1H, d, J=15.1 Hz), 4.05–4.20 (2H, m), 4.29 (1H, dd, J=6.4, 11.7 Hz), 4.45 (1H, dd, J=2.2, 11.7 Hz), 4.89 (1H, d, J=7.4 Hz), 6.75–6.85 (2H, m), 6.85–7.05 (2H, m), 7.05–7.2 (4H, m)

Example 2

2-(4-Methoxybenzyl)phenyl 6-O-methoxycarbonyl-β-D-glucopyranoside

The title compound was prepared in a similar manner to that described in Example 1 using methyl chloroformate instead of ethyl chloroformate.

$^1$H-NMR (CD$_3$OD) δ ppm: 3.30–3.65 (4H, m), 3.71 (3H, s), 3.74 (3H, s), 3.93 (1H, d, J=15.1 Hz), 4.01 (1H, d, J=15.1 Hz), 4.30 (1H, dd, J=6.4, 11.7 Hz), 4.45 (1H, dd, J=2.1, 11.7 Hz), 4.89 (1H, d, J=7.4 Hz), 6.75–6.85 (2H, m), 6.85–7.05 (2H, m), 7.05–7.20 (4H, m)

Example 3

2-(4-Methoxybenzyl)phenyl 6-O-[2-(methoxy)ethyloxy-carbonyl]-β-D-glucopyranoside The title compound was prepared in a similar manner to that described in Example 1 using 2-(methoxy)ethyl chloroformate instead of ethyl chloroformate.

$^1$H-NMR (CD$_3$OD) δ ppm: 3.30–3.65 (9H, m), 3.74 (3H, s), 3.92 (1H, d, J=15.1 Hz), 4.02 (1H, d, J=15.1 Hz), 4.10–4.25 (2H, m), 4.30 (1H, dd, J=6.3, 11.7), 4.47 (1H, dd, J=2.1, 11.7 Hz), 4.89 (1H, d, J=7.4 Hz), 6.70–6.85 (2H, m), 6.85–7.05 (2H, m), 7.05–7.20 (4H, m)

Example 4

2-(4-Methoxybenzyl)phenyl 6-O-hexanoyl-β-D-glucopyranoside

To a solution of 2-(4-methoxybenzyl)phenyl β-D-glucopyranoside (0.10 g) in 2,4,6-trimethylpyridine (2 mL) was added hexanoyl chloride (0.072 g) at 0° C., and the mixture was stirred for 3 hours. To the reaction mixture was added 10% aqueous citric acid solution, and the mixture was extracted with ethyl acetate. The organic layer was washed with 10% aqueous citric acid solution and brine. The organic layer was dried over anhydrous magnesium sulfate, and the solvent was removed under reduced pressure. The residue was purified by preparative thin layer chromatography on silica gel (eluent: dichloromethane/methanol=10/1) to give 2-(4-methoxybenzyl)phenyl 6-O-hexanoyl-β-D-glucopyranoside (0.030 g).

$^1$H-NMR (CD$_3$OD) δ ppm: 0.80–0.95 (3H, m), 1.20–1.35 (4H, m), 1.50–1.65 (2H, m), 2.25–2.35 (2H, m), 3.30–3.65 (4H, m), 3.74 (3H, s), 3.93 (1H, d, 3=15.1 Hz),4.01 (1H, d, J=15.1 Hz),4.22 (1H, dd, J=6.7, 11.8 Hz), 4.42 (1H, dd, J=2.2, 11.8 Hz), 4.85–4.95 (1H, m), 6.75–6.85 (2H, m), 6.85–7.05 (2H, m), 7.05–7.20 (4H, m)

Example 5

2-(4-Methoxybenzyl)phenyl 6-O-propionyl-β-D-glucopyranoside

The title compound was prepared in a similar manner to that described in Example 4 using propionyl chloride instead of hexanoyl chloride.

$^1$H-NMR (CD$_3$OD) δ ppm: 1.08 (3H, t, J=7.6 Hz), 2.25–2.40 (2H, m), 3.30–3.55 (3H, m), 3.55–3.65 (1H, m), 3.74 (3H, s), 3.93 (1H, d, J=15.1 Hz), 4.01 (1H, d, J=15.1 Hz), 4.23 (1H, dd, J=6.7, 11.8 Hz), 4.40 (1H, dd, J=2.1, 11.8 Hz), 4.85–4.95 (1H, m), 6.75–6.85 (2H, m), 6.85–7.05 (2H, m), 7.05–7.20 (4H, m)

Example 6

2-(4-Methoxybenzyl)phenyl 6-O-butyryl-β-D-glucopyranoside

The title compound was prepared in a similar manner to that described in Example 4 using butyryl chloride instead of hexanoyl chloride.

$^1$H-NMR (CD$_3$OD) δ ppm: 0.90 (3H, t, J=7.4 Hz), 1.50–1.70 (2H, m), 2.20–2.35 (2H, m), 3.30–3.65 (4H, m), 3.74 (3H, s), 3.93 (1H, d, J=15.1 Hz), 4.01 (1H, d, J=15.1 Hz), 4.22 (1H, dd, J=6.7, 11.8 Hz), 4.42 (1H, dd, J=2.2, 11.8 Hz), 4.85–4.95 (1H, m), 6.75–6.85 (2H, m), 6.85–7.05 (2H, m), 7.05–7.20 (4H, m)

Example 7

2-(4-Methoxybenzyl)phenyl 6-O-acetyl-β-D-glucopyranoside

The title compound was prepared in a similar manner to that described in Example 4 using acetyl chloride instead of hexanoyl chloride.

$^1$H-NMR (CD$_3$OD) δ ppm: 2.02 (3H, s), 3.30–3.65 (4H, m), 3.74 (3H, s), 3.93 (1H, d, J=15.1 Hz), 4.01 (1H, d, J=15.1 Hz), 4.24 (1H, dd, J=6.5, 11.9 Hz), 4.38 (1H, dd, J=2.2, 11.9 Hz), 4.85–4.95 (1H, m), 6.75–6.85 (2H, m), 6.85–7.05 (2H, m), 7.05–7.20 (4H, m)

Example 8

2-(4-Methoxybenzyl)phenyl 6-O-isobutyryl-β-D-glucopyranoside

The title compound was prepared in a similar manner to that described in Example 4 using isobutyryl chloride instead of hexanoyl chloride.

$^1$H-NMR (CD$_3$OD) δ ppm: 1.11 (3H, d, J=7.0 Hz), 1.12 (3H, d, J=7.0 Hz), 2.45–2.60 (1H, m), 3.30–3.65 (4H, m), 3.74 (3H, s), 3.93 (1H, d, J=15.1 Hz), 4.00 (1H, d, J=15.1 Hz), 4.19 (1H, dd, J=6.9, 11.8 Hz), 4.43 (1H, dd, J=2.1, 11.8

Hz), 4.85–4.95(1H, m), 6.75–6.85 (2H, m), 6.85–7.05 (2H, m), 7.05–7.20 (4H, m)

Example 9

2-(4-Methoxybenzyl)phenyl 6-O-ethylsuccinyl-β-D-glucopyranoside

The title compound was prepared in a similar manner to that described in Example 4 using ethylsuccinyl chloride instead of hexanoyl chloride.

$^1$H-NMR (CD$_3$OD) δ ppm: 1.19 (3H, t, J=7.1 Hz), 2.50–2.70 (4H, m), 3.30–3.65 (4H, m), 3.74 (3H, s), 3.93 (1H, d, J=15.1 Hz), 4.02 (1H, d, J=15.1 Hz), 4.08 (2H, q, J=7.1 Hz), 4.22 (1H, dd, J=6.7, 11.8 Hz), 4.44 (1H, dd, J=2.1, 11.8 Hz), 4.85–4.95(1H, m), 6.75–7.25 (8H, m)

Example 10

2-(4-Methoxybenzyl)phenyl 6-O-isopropyloxycarbonyl-β-D-glucopyranoside

To a solution of isopropanol (0.12 g) in 2,4,6-trimethylpyridine (2 mL) was added triphosgene (0.022 g) at 0° C., and the mixture was stirred for 1 hour. Thereafter, 2-(4-methoxybenzyl)phenyl β-D-glucopyranoside (0.075 g) was added to the reaction mixture, and the mixture was stirred at room temperature overnight. To the reaction mixture was added 10% aqueous citric acid solution, and the mixture was extracted with ethyl acetate. The organic layer was washed with 10% aqueous citric acid solution and water, and dried over magnesium sulfate, and the solvent was removed under reduced pressure. The residue was purified by preparative thin layer chromatography on silica gel (eluent: dichloromethane/methanol=10/1) to give 2-(4-methoxybenzyl)-phenyl 6-O-isopropyloxycarbonyl-β-D-glucopyranoside (0.024 g).

$^1$H-NMR (CD$_3$OD) δ ppm: 1.21 (3H, d, J=6.3 Hz), 1.23 (3H, d, J=6.3 Hz), 3.30–3.65 (4H, m), 3.74 (3H, s), 3.93 (1H, d, J=15.1 Hz), 4.02 (1H, d, J=15.1 Hz), 4.28 (1H, dd, J=6.4, 11.7 Hz), 4.43 (1H, dd, J=2.2, 11.7 Hz), 4.70–4.85 (1H, m), 4.85–4.95(1H, m), 6.75–7.20 (8H, m)

Examples 11–22

The compounds in the following Table 1 were prepared in a similar manner to that described in Example 1 or 2 using a compound obtained in Reference Examples 12–17.

TABLE 1

| Example | R | P |
|---|---|---|
| 11 | Methyl | Ethoxycarbonyl |
| 12 | Methyl | Methoxycarbonyl |
| 13 | Ethyl | Ethoxycarbonyl |
| 14 | Ethyl | Methoxycarbonyl |
| 15 | Isobutyl | Ethoxycarbonyl |
| 16 | Isobutyl | Methoxycarbonyl |
| 17 | Ethoxy | Ethoxycarbonyl |
| 18 | Ethoxy | Methoxycarbonyl |
| 19 | Isopropyl | Ethoxycarbonyl |
| 20 | Isopropyl | Methoxycarbonyl |
| 21 | Ethylthio | Ethoxycarbonyl |
| 22 | Ethylthio | Methoxycarbonyl |

Test Example 1

Assay for Inhibitory Effect on Human SGLT2 Activity

1) Construction of the Plasmid Vector Expressing Human SGLT2

Preparation of the cDNA library for PCR amplification was performed by reverse transcription of a total RNA deprived from human kidney (Ori gene) with oligo dT as the primer, using SUPERSCRIPT Preamplification System (Gibco-BRL: LIFE TECHNOLOGIES). The DNA fragment coding for human SGLT2 was amplified by the Pfu DNA Polymerase (Stratagene)-used PCR reaction, in which the human kidney cDNA library described above was used as the template and the following oligo nucleotides 0702F and 0712R, presented as Sequence Numbers 1 and 2 respectively, were used as the primers. The amplified DNA fragment was ligated into pCR-Blunt (Invitrogen), a vector for cloning, according to standard method of the kit. The competent cell, *Escherichia coli* HB101 (Toyobo), was transformed according to usual method and then selection of the transformants was performed on the LB agar medium containing 50 μg/mL of kanamycin. After the plasmid DNA was extracted and purified from the one of the transformants, amplifying of the DNA fragment coding for human SGLT2 was performed by the Pfu DNA Polymerase (Stratagene)-used PCR reaction, in which the following oligo nucleotides 0714F and 0715R, presented as Sequence Numbers 3 and 4 respectively, were used as the primers. The amplified DNA fragment was digested with restriction enzymes, Xho I and Hind III, and then purified with Wizard Purification System (Promega). This purified DNA fragment was inserted at the corresponding multi-cloning sites of pcDNA3.1 (−) Myc/His-B (Invitrogen), a vector for expressing of fusion protein. The competent cell, *Escherichia coli* HB101 (Toyobo), was transformed according to usual method and then selection of the transformant was performed on the LB agar medium containing 100 μg/mL of ampicillin. After the plasmid DNA was extracted and purified from this transformant, the base sequence of the DNA fragment inserted at the multi-cloning sites of pcDNA3.1 (−) Myc/His-B was analyzed. This clone had a single base substitution (ATC which codes for the isoleucine-433 was substituted by GTC) compared with the human SGLT2 reported by Wells et al (Am. J. Physiol., Vol. 263, pp. 459–465 (1992)). Sequentially, a clone in which valine is substituted for the isoleucine-433 was obtained. This plasmid vector expressing human SGLT2 in which the peptide presented as Sequence Number 5 is fused to the carboxyl terminal alanine residue was designated KL29.

```
ATGGAGGAGCACACAGAGGC            Sequence Number 1

GGCATAGAAGCCCCAGAGGA            Sequence Number 2

AACCTCGAGATGGAGGAGCACACAGAGGC   Sequence Number 3

AACAAGCTTGGCATAGAAGCCCCAGAGGA   Sequence Number 4

KLGPEQKLISEEDLNSAVDHHHHHH       Sequence Number 5
```

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 $\mu$F, 2×10$^6$ cells of COS-7 cell and 20 $\mu$g of KL29 in 500 $\mu$L of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 $\mu$L of this cell suspension was added. After overnight culture at 37° C. under 5% $CO_2$, 125 $\mu$L of DMEM medium which is containing 10% of fetal bovine serum (Sanko Jyunyaku), 100 units/mL sodium penicillin G (Gibco-BRL: LIFE TECHNOLOGIES) and 100 $\mu$g/mL streptomycin sulfate (Gibco-BRL: LIFE TECHNOLOGIES) was added to each well. After a culture until the following day, these cells were used for the measurement of the inhibitory activity against the uptake of methyl-$\alpha$-D-glucopyranoside.

3) Measurement of the Inhibitory Activity Against the Uptake of Methyl-$\alpha$-D-Glucopyranoside After a test compound was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-$\alpha$-D-glucopyranoside, 10 mM 2-[4-(2-hydroxyethyl)-1-piperazinyl]ethane sulfonic acid and 5 mM tris (hydroxymethyl) aminomethane), each diluent was used as test sample for measurement of the inhibitory activity. After removal of the medium of the COS-7 cells expressing transiently human SGLT2, to each well 200 $\mu$L of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1piperazinyl]-ethane sulfonic acid and 5 mM tris (hydroxymethyl) aminomethane) was added, and the cells were incubated at 37° C. for 10 minutes. After the pretreatment buffer was removed, 200 $\mu$L of the same buffer was added again, and the cells were incubated at 37° C. for 10 minutes. The buffer for measurement was prepared by adding of 7 $\mu$L of methyl-$\alpha$-D-(U-14C)glucopyranoside (Amersham Pharmacia Biotech) to 525 $\mu$L of the prepared test sample. For the control, the buffer for measurement without test compound was prepared. For estimate of the basal uptake in the absence of test compound and sodium, the buffer for measurement of the basal uptake, which contains 140 mM choline chloride in place of sodium chloride, was prepared similarly. After the pretreatment buffer was removed, 75 $\mu$L of the buffer for measurement was added to each well, and the cells were incubated at 37° C. for 2 hours. After the buffer for measurement was removed, 200 $\mu$L of the washing buffer (a pH 7.4 buffer containing 140 mM choline chloride, 2 mM potassium chloride, 1 mM calcium chloride, 1 mM magnesium chloride, 10 mM methyl-$\alpha$-D-glucopyranoside, 10 mM 2-[4-(2-hydroxyethyl)-1-piperazinyl]ethane sulfonic acid and 5 mM tris(hydroxymethyl)aminomethane) was added to each well and immediately removed. After two additional washing, the cells were solubilized by addition of 75 $\mu$L of 0.2 N sodium hydroxide to each well. After the cell lysates were transferred to the PicoPlate (Packard) and 150 $\mu$L of MicroScint-40 (Packard) was added, the radioactivity was measured with microplate scintillation counter TopCount (Packard). The difference in uptake was obtained as 100% value by subtracting the radioactivity in the basal uptake from that in control and then the concentrations at which 50% of uptake was inhibited ($IC_{50}$ Value) were calculated from the concentration-inhibition curve by least square method. The results are shown in the following Table 2.

TABLE 2

| Test compound | $IC_{50}$ value (nM) |
| --- | --- |
| Reference Example 11 | 350 |
| Reference Example 12 | 450 |
| Reference Example 13 | 140 |
| Reference Example 14 | 500 |
| Reference Example 15 | 330 |
| Reference Example 16 | 370 |
| Reference Example 17 | 110 |

Test Example 2

Assay for Oral Absorbability

1) Preparation of the Samples for Measurement of the Drug Concentration After Intravenous Injection to the Tail Vein As experimental animal, overnight fasted SD rats (CLEA JAPAN, INC., male, 5 weeks of age, 140–170 g) were used. Sixty mg of a test compound was suspended or dissolved in 1.8 mL of ethanol and then dissolved by adding 7.2 mL of polyethylene glycol 400 and 9 mL of saline to prepare a 3.3 mg/mL solution. The body weights of rats were measured and then the solution of the test compound was intravenously injected to the tail vein of unanesthetized rats at the dose of 3 mL/kg (10 mg/kg). The intravenous injection to the tail was performed with 26 G injection needle and 1 mL syringe. The sampling times for collection of blood were 2, 5, 10, 20, 30, 60 and 120 minutes after the intravenous injection to the tail vein. The blood was centrifuged and the plasma was used as the sample for measurement of the drug concentration in blood.

2) Preparation of the Samples for Measurement of the Drug Concentration After Oral Administration As experimental animal, overnight fasted SD rats (CLEA JAPAN, INC., male, 5 weeks of age, 140–170 g) were used. A test compound was suspended or dissolved in 0.5% sodium carboxymethylcellulose solution at the concentration of 1 mg/mL of active form. After the body weights of rats were measured, the liquid containing the test compound described above was orally administered at the dose of 10 mL/kg (10 mg/kg as active form). The oral administration was performed with gastric tube for rat and 2.5 mL syringe. The sampling times for collection of blood were 15, 30, 60, 120 and 240 minutes after the oral administration. The blood was centrifuged and the plasma was used as the sample for measurement of the drug concentration in blood.

3) Measurement of Drug Concentration

To 0.1 mL of the plasma obtained in 1) and 2) described above, 1 μg of 2-(4-ethoxybenzyl)phenyl β-D-glucopyranoside described in Reference Example 15 was added as internal standard and then deproteinization was performed by adding 1 mL of methanol. After centrifugation, the methanol phase was evaporated to dryness under a stream of nitrogen. The residue was dissolved in 300 μL of the mobile phase and a 30 μL aliquot of the solution was injected into HPLC. The drug concentration in plasma was analysed by HPLC method under the condition as follows.

Column: Inertsil ODS-2 (4.6×250 mm)
Mobile Phase: Acetonitrile/10 mM Phosphate buffer (pH 3.0)=25:75(v/v)
Column Temperature: 50° C.
Flow Rate: 1.0 mL/minute
Wavelength for Measurement: UV 232 nm After addition of 1 μg of 2-(4-ethoxybenzyl)phenyl β-D-glucopyranoside described in Reference Example 15 as internal standard and each concentration (1.0, 0.5, 0.2, 0.1, 0.05 and 0.02 μg) of 2-(4-methoxybenzyl)phenyl β-D-glucopyranoside described in Reference Example 11 to 0.1 mL of the blank plasma, similar operating described above was performed and then the standard curve was prepared.

Each area under the plasma concentration-time curve by intravenous injection to the tail vein and oral administration of test compound was estimated with WinNonlin Standard made by Pharsight Corporation from the plasma concentrations at each time obtained from HPLC and then the bioavailability (%) was calculated by the formula as follows. The results are shown in the following Table 3.

TABLE 3

$$\text{Bioavailability}(\%) = \frac{\text{Area under the Plasma Concentration - Time Curve by Oral Administration}}{\text{Area under the Plasma Concentration - Time Curve by Intravenous Injection to the Tail Vein}} \times 100$$

| Test compound | Bioavailability (%) |
| --- | --- |
| Example 1 | 46 |
| Example 4 | 61 |
| Reference Example 11 | 15 |

Test Example 3

Assay for the Facilitatory Effect on Urinary Glucose Excretion

As experimental animal, non-fasted SD rats (SLC. Inc., male, 8 weeks of age, 270–320 g) were used. A test compound was suspended in 0.5% sodium carboxymethylcellulose solution and 0.3, 1 and 3 mg/mL suspension were prepared. Adler the body weights of rats were measured, the test suspension was orally administered at the dose of 10 mL/kg (3, 10 and 30 mg/kg). For the control, just only 0.5% sodium carboxymethylcellulose solution was orally administered at the dose of 10 mL/kg. The oral administration was performed with gastric tube for rat and 2.5 mL syringe. The head count in one group was 5 or 6. Collection of urine was performed in metabolic cage after the oral administration was finished. The sampling time for collection of urine was 24 hours after the oral administration. After collection of urine was finished, the urine volume was recorded and the urinary glucose concentration was measured. The glucose concentration was measured with a kit for laboratory test: Glucose B-Test WAKO (Wako Pure Chemical Industries, Ltd.). The amount of urinary glucose excretion in 24 hours per 200 g of body weight was calculated from urine volume, urinary glucose concentration and body weight. The results are shown in the following Table 4.

TABLE 4

| Test compound | Dose (mg/kg) | Amount of Urinary Glucose Excretion (mg/24 hours · 200 g body weight) |
| --- | --- | --- |
| Example 1 | 3 | 52 |
| | 10 | 239 |
| | 30 | 513 |

Test Example 4

Acute Toxicity Test

Four weeks old male ICR mice (CLEA JAPAN, INC. 22–28 g, 5 animals in each group) were fasted for 4 hours, and 60 mg/mL of a suspension of a test compound in 0.5% sodium carboxymethylcellulose solution was orally administered at the dose of 10 mL/kg(600 mg/kg). No death was observed until 24 hours after the administration as shown in the following Table 5.

TABLE 5

| Test compound | Death number |
| --- | --- |
| Example 1 | 0/5 |

Industrial Applicability

The glucopyranosyloxybenzylbenzene derivatives represented by the above general formula (I) of the present invention have an improved oral absorption and can exert an excellent inhibitory activity in human SGLT2 by converting into glucopyranosyloxybenzylbenzene derivatives represented by the above general formula (II) as active forms thereof in vivo after oral administration. The present invention can provide agents for the prevention or treatment of a disease associated with hyperglycemia such as diabetes, diabetic complications, obesity or the like, which are also suitable as oral formulations.

What is claimed is:
1. A glucopyranosyloxybenzylbenzene derivative represented by the general formula:

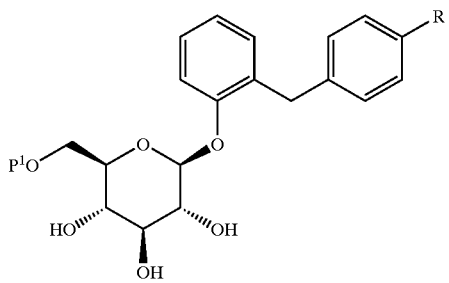

wherein R represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group; and $P^1$ represents a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group.

2. A glucopyranosyloxybenzylbenzene derivative as claimed in claim 1, represented by the general formula:

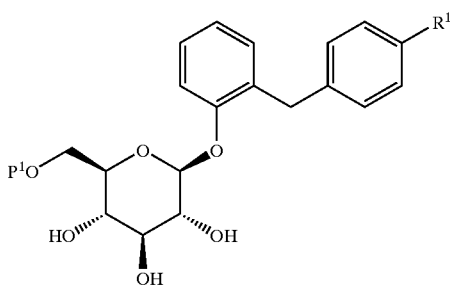

wherein $R^1$ represents a lower alkyl group or a lower alkoxy group; and $P^1$ represents a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group.

3. A glucopyranosyloxybenzylbenzene derivative as claimed in claim 1, represented by the general formula:

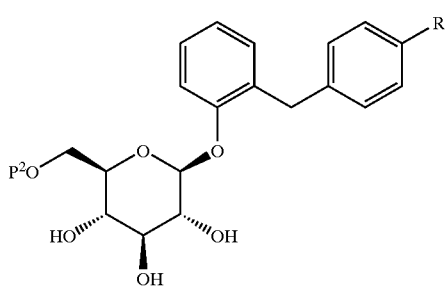

wherein R represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group; and $P^2$ represents a lower acyl group or a lower alkoxycarbonyl group.

4. A glucopyranosyloxybenzylbenzene derivative as claimed in claim 2, represented by the general formula:

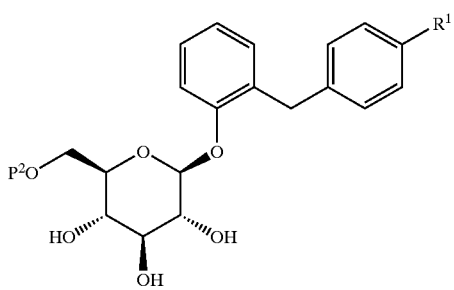

wherein $R^1$ represents a lower alkyl group or a lower alkoxy group; and $P^2$ represents a lower acyl group or a lower alkoxycarbonyl group.

5. The glucopyranosyloxybenzylbenzene derivative as claimed in claim 4, represented by the formula:

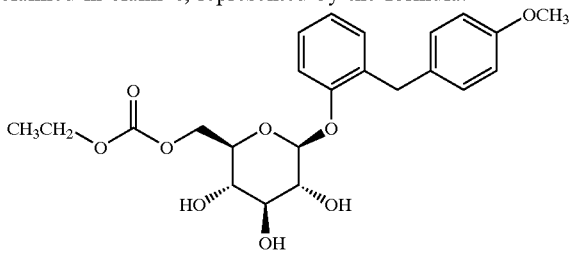

6. The glucopyranosyloxybenzylbenzene derivative as claimed in claim 4, represented by the formula:

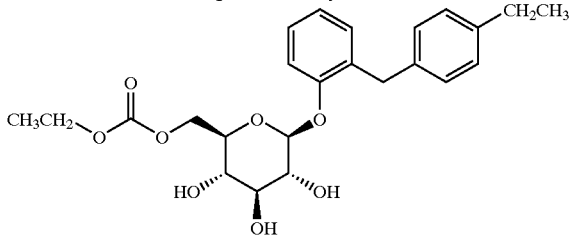

7. A glucopyranosyloxybenzylbenzene derivative as claimed in claim 3, wherein $P^2$ represents the lower alkoxycarbonyl group.

8. A glucopyranosyloxybenzylbenzene derivative as claimed in claim 4, wherein $P^2$ represents the lower alkoxycarbonyl group.

9. A pharmaceutical composition comprising as the active ingredient a glucopyranosyloxybenzylbenzene derivative as claimed in claim 1, in combination with a pharmaceutical additive.

10. A pharmaceutical composition as claimed in claim 9 wherein the composition is an oral formulation.

11. A method for the treatment of a disease associated with hyperglycemia, which comprises administering a therapeutically effective amount of a glucopyranosyloxybenzylbenzene derivative as claimed in claim 1 to a patient in need of treatment of a disease associated with hyperglycemia.

12. A method as claimed in claim 11 wherein the glucopyranosyloxybenzylbenzene derivative is a human SGLT2 inhibitor.

13. A method as claimed in claim 11 wherein the disease associated with hyperglycemia is diabetes or diabetic complications.

14. A method as claimed in claim 11 wherein the disease associated with hyperglycemia is obesity.

* * * * *